US010813583B2

(12) United States Patent
Kaji

(10) Patent No.: US 10,813,583 B2
(45) Date of Patent: Oct. 27, 2020

(54) SLEEP STATE PREDICTION DEVICE

(71) Applicant: TOYOTA JIDOSHA KABUSHIKI KAISHA, Toyota-shi (JP)

(72) Inventor: Hirotaka Kaji, Hadano (JP)

(73) Assignee: TOYOTA JIDOSHA KABUSHIKI KAISHA, Toyota-shi (JP)

( * ) Notice: Subject to any disclaimer, the term of this patent is extended or adjusted under 35 U.S.C. 154(b) by 54 days.

(21) Appl. No.: 15/464,738

(22) Filed: Mar. 21, 2017

(65) Prior Publication Data
US 2017/0273617 A1 Sep. 28, 2017

(30) Foreign Application Priority Data

Mar. 24, 2016 (JP) ................................ 2016-059972

(51) Int. Cl.
*A61B 5/00* (2006.01)
*A61B 5/113* (2006.01)
(Continued)

(52) U.S. Cl.
CPC .......... *A61B 5/4812* (2013.01); *A61B 5/0205* (2013.01); *A61B 5/11* (2013.01);
(Continued)

(58) Field of Classification Search
None
See application file for complete search history.

(56) References Cited

U.S. PATENT DOCUMENTS

2004/0073128 A1* 4/2004 Hatlestad ............. A61B 5/0809
600/533
2005/0080349 A1 4/2005 Okada et al.
(Continued)

FOREIGN PATENT DOCUMENTS

CN 105286823 A 2/2016
JP 2005-118151 A 5/2005
(Continued)

OTHER PUBLICATIONS

M. Sugiyama and Jaak Simm, "A computationally-efficient alternative to kernel logistic regression," 2010 IEEE International Workshop on Machine Learning for Signal Processing, Kittila, 2010, pp. 124-129. doi: 10.1109/MLSP.2010.5589255.*
(Continued)

*Primary Examiner* — Christopher Koharski
*Assistant Examiner* — James Moss
(74) *Attorney, Agent, or Firm* — Oblon, McClelland, Maier & Neustadt, L.L.P.

(57) ABSTRACT

A device of the disclosure determines to which of a plurality of sleep stages in a sleep state including a wake stage a sleep state of a subject belongs, based on a sleep state function that is calculated using as variables a respiratory motion feature and a body motion feature that are respectively extracted from respiratory motion index values and body motion index values of the subject measured in time series. The sleep state function is a function including coefficient parameters that are set based on learning data including sleep stage determination results by a measurement of a sleep state for calibration, and respiratory motion features and body motion features that are measured simultaneously with the measurement for calibration.

20 Claims, 5 Drawing Sheets

(51) Int. Cl.
  *A61B 5/0205* (2006.01)
  *A61B 5/11* (2006.01)
(52) U.S. Cl.
  CPC .......... *A61B 5/1135* (2013.01); *A61B 5/4809* (2013.01); *A61B 5/6823* (2013.01); *A61B 5/6892* (2013.01); *A61B 5/7267* (2013.01); *A61B 5/113* (2013.01); *A61B 5/725* (2013.01); *A61B 5/7207* (2013.01); *A61B 2560/0223* (2013.01); *A61B 2562/0219* (2013.01); *A61B 2562/0247* (2013.01)

(56) References Cited

U.S. PATENT DOCUMENTS

| | | | |
|---|---|---|---|
| 2005/0209643 A1* | 9/2005 | Heruth | A61B 5/02 607/3 |
| 2006/0009704 A1 | 1/2006 | Okada et al. | |
| 2006/0169282 A1 | 8/2006 | Izumi et al. | |
| 2007/0015976 A1* | 1/2007 | Miesel | A61B 5/0006 600/301 |
| 2012/0179061 A1* | 7/2012 | Ramanan | A61M 16/024 600/538 |
| 2013/0254143 A1 | 9/2013 | Ueki et al. | |
| 2013/0310712 A1 | 11/2013 | Kanemitsu et al. | |
| 2015/0190086 A1* | 7/2015 | Chan | H05K 999/99 600/301 |
| 2015/0230750 A1* | 8/2015 | McDarby | A61B 5/0816 600/407 |
| 2018/0014784 A1* | 1/2018 | Heeger | A61B 5/0006 |

FOREIGN PATENT DOCUMENTS

| | | |
|---|---|---|
| JP | 2006-20810 | 1/2006 |
| JP | 2006-280686 | 10/2006 |
| JP | 2009-172197 A | 8/2009 |
| JP | 2011-15887 A | 1/2011 |
| JP | 2015-532855 A | 11/2015 |
| WO | WO 2012/077476 A1 | 6/2012 |
| WO | WO 2012/114588 A1 | 8/2012 |
| WO | WO 2014/047310 A1 | 3/2014 |

OTHER PUBLICATIONS

Parthasarathy S, Mehta S., and Srinivasan S. (2006). Robust Periodicity Detection Algorithms, Proceedings of the 15th ACM international conference on Information and knowledge management, ftp://ftp.cse.ohio-state.edu/pub/tech-report/2006/TR29.pdf, viewed on Feb. 7, 2019.*
Talat Ozyagcilar, "Using the Xtrinsic FXOS8700CQ Accelerometer and Magnetometer Vector-Magnitude Function Function", https://www.nxp.com/docs/en/application-note/AN4458.pdf), Jun. 2012, viewed on Feb. 6, 2019.*
Vernier, "3-Axis Accelerometer", http://www.vernier.cz/katalog/manualy/en/3d-bta.pdf, Mar. 4, 2014, viewed on Feb. 6, 2018.*
Carskadon, M. A., Dement, W. C., Mitler, M. M., Roth, T., Westbrook, P. R. and Keenan, S. Guidelines for the multiple sleep latency test (MSLT): a standard measure of sleepiness. Sleep, 1986, 9: 519-524.*
Fabio Pizza et al., "Different sleep onset criteria at the multiple sleep latency test (MSLT): an additional marker to differentiate central nervous system (CNS) hypersomnias", Journal of Sleep Research vol. 20 Issue 1pt2 Mar. 2011, pp. 250-256.*
Masashi Sugiyama et al., "A Computationally-Efficient Alternative to Kernel Logistic Regression", IEEE IWSML 2012, 1-10.*
A Roebuck et al., "A review of signals used in sleep analysis", Physiol Meas. Jan. 2014; 35(1): R1-57., Published online Dec. 17, 2013. doi: 10.1088/0967-3334/35/1/R1, https://www.ncbi.nlm.nih.gov/pmc/articles/PMC4024062/,viewed on Feb. 6, 2019.*
Walter Karlen, et al., "Improving Actigraph Sleep/Wake Classification with Cardio-Respiratory Signals", IEEE EMBC, 2008, 4 pages.
Masashi Sugiyama, et al., "Least-Squares Probabilistic Classifier: A Computationally Efficient Alternative to Kernel Logistic Regression", Proceedings of International Workshop on Statistical Machine Learning for Speech Processing, 2012, 10 pages.
Alexander Tataraidze, et al., "Sleep Stage Classification Based on Respiratory Signal", IEEE EMBC, 2015, 4 pages.
"Robust period detection algorithms", Parthasarathy S et. al, Proceedings of the 15th ACM international conference on information and knowledge management, pp. 874-875, Dec. 2006.
"Using the Xtrinsic FXLS8471Q Accelerometer vector-magnitude function", Talat Ozyagcilar, pp. 1-7, Dec. 2013.

* cited by examiner

RELATED ART

SLEEP STATE PREDICTION DEVICE

INCORPORATION BY REFERENCE

The disclosure of Japanese Patent Application No. 2016-059972 filed on Mar. 24, 2016 including the specification, drawings and abstract is incorporated herein by reference in its entirety.

BACKGROUND

1. Technical Field

The disclosure relates to a device that predicts a sleep state of a human being. More specifically, the disclosure relates to a device that predicts a sleep stage of a subject based on measured data of respiratory waveform and so on of the subject.

2. Description of Related Art

Since the sleep state (depth of sleep) of a human being becomes important information on health care, there have been proposed various techniques for determining the sleep state of a human being. It is known that the sleep state can be classified into, for example, Rapid Eye Movement (REM) sleep stage and non-REM sleep stages I~IV (sleep stages). In a determination of the sleep stage, in principle, according to the R&K method as the international determination standard, brain wave, electrocardiogram, respiration, electrooculoram, and electromyogram near a jaw of a subject are simultaneously measured using polysomnography (PSG), and then, an expert determines the sleep stage per 30 seconds by referring to a series of measured data (see FIG. 5A). However, since the data measurement by PSG requires a large-scale facility, the determination of the sleep stage by PSG is normally carried out in a hospital or the like and cannot easily be used by an ordinary person. Therefore, in recent years, there have been proposed various techniques that measure a respiratory motion (displacement of body surface due to respiration) or a body motion of a subject in bed or at rest using a wristband-type or band-type wearable pressure sensor or acceleration sensor (wearable sensor), thereby predicting whether or not the subject is in a sleep state, or in which of sleep stages the subject is, based on the measured data.

As such a technique, for example, in Japanese Patent Application Publication No. 2006-20810 (JP 2006-20810 A) and Japanese Patent Application Publication No. 2006-280686 (JP 2006-280686 A), there is proposed a configuration in which, using a pressure sensor that is worn on the body of a subject or that is inserted under the body of a lying subject, the displacement of the body surface of the subject is measured as a pressure change, and based on characteristics of waveform in time-series data of the measured pressure changes, a sleep state of the subject is predicted. In the case of these documents, to give a brief description, the occurrence of a body motion of the subject is predicted in a region where the amplitude of waveform in time-series data of the measured pressures becomes relatively large, and a determination is made such that the subject is in a wake state in a region where the body motion is detected, or when the body motion exceeds a predetermined time. In Proc. IEEE EMBC (Walter Karlen, Claudio Mattiussi, Dario Floreano. Improving Actigraph Sleep/Wake Classification with Cardio-Respiratory Signals, Proc. IEEEEMBC 2008 p. 5262-6265), there is disclosed an attempt to distinguish between a wake state and a sleep state by wearing on a subject a sensor device in which sensors for measuring heartbeat, respiration, motion, acceleration, and temperature are incorporated, and inputting feature values of the obtained measured values into a neutral network. In this document, it is described that, by referring to the heartbeat and the respiratory motion when the body motion measured by an acceleration sensor (actigraph) is small, it is possible to improve the detection accuracy when the subject is in the wake state.

SUMMARY

According to the technique using the wearable sensor, it is possible to predict a sleep state of a human being with a certain accuracy based on the measured data about the respiratory state or the body motion of a human being without using PSG. However, the correspondence relationship between the waveform in the time-series data of the pressure changes (hereinafter referred to as "respiratory waveform") due to the displacement of the body surface caused by the respiratory motion of the subject that is obtained by the pressure sensor, the acceleration due to the body motion of the subject that is obtained by the acceleration sensor or the like, and the sleep state and/or the sleep stage is complicated. Therefore, it is difficult to accurately predict the sleep state or the sleep stage based on whether or not a certain feature in the respiratory waveform or the body motion exceeds a predetermined threshold value. For example, when the occurrence of a large body motion of a subject is detected, or when the continuation of a large body motion of a subject over a predetermined time is detected, there is a high possibility that the subject is in a wake state, but such a body motion may occur even when the subject is in a sleep state, while, conversely, the subject may be in a wake state when there is no such a large body motion. Likewise, when it is determined to which of a plurality of sleep stages in a sleep state the state of a subject belongs, it is difficult to accurately specify the sleep stage of the subject by a magnitude relation between a value of a certain feature extracted from measured data and a predetermined threshold value. Further, relatively much noise is included in measured data (signal) that is obtained by a wearable sensor, and therefore, when the number of features extracted from the measured data is small, it may occur that the determination result (prediction result) is not stable due to the influence of noise.

Therefore, in a device that predicts a sleep state and/or a sleep stage of a human being based on features extracted from measured data about a respiratory motion and a body motion of a human being who is measured using a wearable sensor, the disclosure can obtain further accurate prediction result of the sleep state and/or the sleep stage. As described above, since a determination of a sleep stage is made via PSG based on the international determination standard, a determination of a sleep stage based on a respiratory motion and a body motion is a prediction of the sleep stage. Therefore, when referred to as "determination of sleep stage" in the description about the aspect of the disclosure, it may be synonymous with "prediction of sleep stage" unless otherwise stated. Further, when referred to as "sleep state" or "sleep stage", it may include a state in which a subject is woken (wake state, wake stage), unless otherwise stated.

A sleep state prediction device according to a first aspect of the disclosure includes a respiratory motion measurement unit configured to measure, in time series, respiratory motion index values indicating a respiratory motion state of a subject, a body motion measurement unit configured to measure, in time series, body motion index values indicating a body motion state of the subject, simultaneously with measurement of the respiratory motion state; a respiratory motion feature extraction unit configured to extract a respiratory motion feature from time-series data of the measured respiratory motion index values; a body motion feature extraction unit configured to extract a body motion feature from time-series data of the measured body motion index values; and a sleep stage determination unit configured to determine to which of a plurality of sleep stages in a sleep state including a wake stage a sleep state of the subject belongs, based on a sleep state value that is calculated by a sleep state function using the respiratory motion feature and the body motion feature as variables, wherein the sleep state function is adjusted by a learning process using, as training data, data groups including sleep stage determination results by a measurement of a sleep state for calibration, and respiratory motion features and body motion features that are respectively extracted from respiratory motion index values and body motion index values measured simultaneously with the measurement for calibration.

In the above-described configuration, "respiratory motion index value" is an index value that indicates a respiratory motion, i.e. a state of a contraction/expansion motion of the chest and/or abdomen of the subject caused by respiration, and typically, may be a pressure that changes due to the displacement of the body surface caused by the respiratory motion of the subject. Therefore, "respiratory motion measurement unit" may be a pressure sensor that is worn on or in contact with the chest or abdomen of the subject. The respiratory motion index value may be a pressure value that is measured by the pressure sensor and that changes due to the displacement of the body surface caused by the respiratory motion of the subject. As described above, the respiratory motion index values are measured in time series and are typically obtained as data that indicates time-series pressure changes. In this case, the waveform of such pressure changes becomes "respiratory waveform". "body motion index value" is an index value that indicates a body motion of the subject, i.e. a motion (change in position/direction) of the body and/or its part. Such a body motion may be detected by an arbitrary technique. In an embodiment of the disclosure, "body motion index value" may be an acceleration value that changes due to the body motion of the subject. Therefore, "body motion measurement unit" may include an acceleration sensor that is worn on or in contact with the body of the subject, and the body motion index value may be an acceleration value that is measured by the acceleration sensor and that changes due to the body motion of the subject. When the acceleration sensor is employed for measuring the body motion index value, it is advantageous in that not only the presence/absence of the body motion, but also the magnitude of the body motion can be measured, so that it is possible to obtain information that can be used when predicting the sleep state in detail. As the acceleration sensor, in order to make it possible to detect the body motion in an arbitrary direction, a sensor that can measure the acceleration in mutually independent three-axis directions may be employed.

In the above-described configuration, "respiratory motion feature" and "body motion feature" may be arbitrary amounts that are extracted from time-series data of "respiratory motion index values" and time-series data of "body motion index values" and are confirmed to have a correlation to the sleep state of the subject. Typically, "respiratory motion feature" and "body motion feature" are not instantaneous values of "respiratory motion index value" and "body motion index value", but the statistics of time-series measured data over a predetermined time interval (epoch). Therefore, the respiratory motion feature extraction unit and the body motion feature extraction unit may be configured to respectively extract the respiratory motion feature and the body motion feature per epoch, and the sleep stage determination unit may be configured to determine the sleep stage of the subject per epoch. As specific examples that are correlated to the sleep state of the subject, it has been found that, in the embodiment of the disclosure, a set of values called "mean respiratory rate", "respiratory coefficient of variation", "amplitude coefficient of variation", and "autocorrelation peak ratio" per epoch in the time-series measured data of the respiratory motion index values can be advantageously employed as the respiratory motion feature, while the maximum value of values called "acceleration difference norms" per epoch in the time-series measured data of the body motion index values can be advantageously employed as the body motion feature (the definitions of these values will be described in a later-described column of embodiment). Further, it has been found that values obtained by subtracting medians of the corresponding features in one-time execution of sleep state prediction from "respiratory coefficient of variation", "amplitude coefficient of variation", "autocorrelation peak ratio", and "maximum value of acceleration difference norms" per epoch (normalization of the features) can be more advantageously employed as "respiratory motion feature" and "body motion feature". Features other than the features listed above may be included in "respiratory motion feature" and "body motion feature", respectively. Also in this case, values obtained by subtracting medians of values of the corresponding features in one-time execution of sleep state prediction from values of the features obtained per epoch from measured data may be used as "respiratory motion feature" and "body motion feature". As described above, when a relatively large number of the amounts (e.g. five or more amounts), compared to the conventional similar devices, are used as the features that are referred to for determining the sleep stage, noise in the measured data hardly affects the determination of the sleep stage, so that the determination result is expected to be stable.

Further, as described above, "sleep state function" is a function that is calculated using both "respiratory motion feature" and "body motion feature" as variables. The sleep state function is a function that is adjusted by a learning process using, as training data, learning data, i.e. "data groups including sleep stage determination results by a measurement of a sleep state for calibration, and respiratory motion features and body motion features that are respectively extracted from respiratory motion index values and body motion index values measured simultaneously with the measurement for calibration". Herein, "a measurement of a sleep state for calibration" is a measurement which gives a result that is allowed as a correct sleep stage determination result in the device of the disclosure, and is typically a measurement by PSG, but is not limited to this. Herein, "learning process" may be an arbitrary process that adjusts "sleep state function" such that when "respiratory motion feature" and "body motion feature" are obtained as variables, it is possible to determine, as accurately as possible, to which of a plurality of sleep stages in a sleep state including a wake stage the sleep state of the subject belongs. More specifically, "learning process" may be a process that sets or searches out a coefficient parameter to be included in a sleep state function such that it becomes possible to determine the sleep stage as accurately as possible by referring to "sleep state value" that is calculated when "respiratory motion feature" and "body motion feature" are input as variables into "sleep state function".

According to the above-described aspect, a determination of the sleep stage of the subject is made based on a sleep state value that is calculated by a sleep state function, adjusted by a learning process (so as to make it possible to determine the sleep stage as accurately as possible), using a respiratory motion feature and a body motion feature as variables. That is, the device of the disclosure is not configured to determine to which of a plurality of sleep stages the sleep state of the subject belongs by separately referring to a respiratory motion feature and a body motion feature in turn as in the conventional similar devices, but is configured to calculate a sleep state value using a sleep state function by comprehensively referring to a respiratory motion feature and a body motion feature, thereby determining the sleep stage of the subject based on that sleep state value. According to this configuration, it is prevented that the sleep stage is determined by a magnitude relation between one feature and a threshold value corresponding thereto, and therefore, for example, it is expected to be able to accurately detect a case where the subject is in a sleep state (not in a wake state) even when there is a body motion, or a case where the subject is in a wake state even when there is no body motion. Further, even when an increase/decrease of one feature is not necessarily in one-to-one correspondence with transition of the sleep stage, in the configuration of the disclosure, since all features can be comprehensively evaluated, it is expected that the sleep stage can be determined accurately compared to the conventional similar devices.

In the above-described aspect, it may be configured that the sleep state value that is calculated by the sleep state function using the respiratory motion feature and the body motion feature as variables is, more specifically, a sleep state value that is calculated for each of a plurality of sleep stages and that is a sleep stage appearance probability indicating a probability that the sleep state of the subject belongs to each sleep stage in a state where the respiratory motion feature and the body motion feature are obtained, and that the sleep stage determination unit determines as the sleep state of the subject the sleep stage of which the sleep stage appearance probability determined by the respiratory motion feature and the body motion feature is the highest in the plurality of sleep stages. As described above, the correspondence relationship between the respiratory motion feature/the body motion feature and the sleep state or the sleep stage is complicated. Accordingly, when a limited number of respiratory motion features and body motion features are obtained, it is often difficult to specify the sleep state of the subject in that state to one sleep stage with an accuracy of 100%. Rather, in a certain state specified by a respiratory motion feature and a body motion feature, there is a possibility that the sleep state of the subject belongs to each of the sleep stages. While the stages are set (discretely) in the sleep state of a human being in the international determination standard, the actual transition of the human sleep state is continuous, and therefore, there is a possibility that the stage cannot be determined clearly.

Therefore, in the above-described aspect, as described above, when a certain respiratory motion feature and a certain body motion feature are obtained, the probabilities (sleep stage appearance probabilities) when the sleep state of the subject on that occasion belongs to each of the plurality of sleep stages may be calculated, and then, the sleep stage with the highest probability in the sleep stage appearance probabilities of the plurality of sleep stages may be determined to be the sleep state of the subject on that occasion.

That is, in a state specified by a certain respiratory motion feature and a certain body motion feature, the sleep stage with the highest certainty is output as a sleep stage prediction result in that state. According to this configuration, while one sleep stage is shown as an prediction result of the device, the certainty of the prediction result can also be grasped. In this regard, depending on the case, while it is possible to specify the maximum value of the calculated sleep stage appearance probabilities of the plurality of sleep stages, it may occur that the maximum value is not so high (e.g. on the way of transition of the sleep stage, it may occur that the appearance probability of each sleep stage does not become outstanding). In such a case, if the sleep stage of the subject is somehow specified to one sleep stage, the prediction accuracy may be degraded. Therefore, in the device of the disclosure, the sleep stage determination unit may be configured to determine that the sleep state of the subject is unclear when the sleep stage appearance probability of the sleep stage with the highest sleep stage appearance probability does not exceed a predetermined value. Since the sum of sleep stage appearance probabilities of non-REM sleep stages in the plurality of sleep stages indicates the appearance probability of the non-REM sleep stages, when this sum becomes large, it can be determined that the subject has fallen asleep. Therefore, the sleep stage determination unit may be configured to predict a falling-asleep time of the subject based on the sum of the sleep stage appearance probabilities of the non-REM sleep stages in the plurality of sleep stages.

As described above, in the configuration in which the sleep stage appearance probabilities of the plurality of sleep stages are calculated as the sleep state values by the sleep state function using the respiratory motion feature and the body motion feature as variables, and then, the sleep stage with the highest probability is determined to be the sleep state of the subject on that occasion, the theory of the least-squares probabilistic classifier (Sugiyama et al., "LEAST-SQUARES PROBABILISTIC CLASSIFIER: A COMPUTATIONALLY EFFICIENT ALTERNATIVE TO KERNEL LOGISTIC REGRESSION" Proceedings of International Workshop on Statistical Machine Learning for Speech Processing (IWSML 2012), pp. 1-10, Kyoto, Japan, Mar. 31, 2012) can be suitably used as the technique of the learning process for adjusting the sleep state function. Therefore, in the above-described aspect, as will be described in more detail in the later-described column of embodiment, the adjustment of the sleep state function may be performed according to the theory of the least-squares probabilistic classifier using the training data. In the least-squares probabilistic classifier, to give a brief description, in a space spanned with variables, a basis function of the type in which a value increases as the distance from an arbitrary point to a point of the training data decreases is set around each point of the training data. This basis function corresponds to a function that indicates the degree of approximation to a state of a point of the training data, and in the learning process, coefficient parameters of the basis function are set. The learning process for the sleep state function is executed before actually carrying out the prediction of the sleep state of the subject by the device of the disclosure (e.g. before shipment of the device), and coefficient parameters to be used in the sleep state function are stored in advance in a memory or the like of the device.

In the above-described aspect, as described above, typically, the sleep stage determination result obtained from the respiratory motion feature and the body motion feature may be output per epoch. However, the transition of the sleep state in the sleep stage determination result that is output per epoch in the device of the disclosure often appears slightly harder or unnaturally compared to actual transition of the sleep state of the subject. Therefore, the sleep stage determination unit may be configured to apply a median filtering process to time-series sleep stages each determined per epoch, and to determine the obtained sleep stage to be the final sleep stage of each epoch.

In the above-described aspect, the time-series pressure value data measured by the pressure sensor includes noise components due to a cause other than the pressure change due to the displacement of the body surface caused by the respiratory motion of the subject. If a respiratory motion feature extracted from the pressure value data including the noise components is used, there is a possibility that the sleep stage determination accuracy is lowered. Therefore, in the above-described aspect, a unit (filter unit) may be provided to extract, from time-series pressure value data measured by the pressure sensor, time-series data of a component of a pressure change due to the displacement of the body surface caused by the respiratory motion of the subject, and the respiratory motion feature extraction unit may be configured to extract a respiratory motion feature from the extracted time-series data of the component of the pressure change. In the embodiment, the filter unit may be a band-pass filter that extracts components in a band of 0.1 Hz to 0.5 Hz, a moving average filter, a low-pass filter, or an arithmetic filter that computes a difference of waveform.

In general, it is known that the possibilities of appearance of the sleep stages in the sleep state change depending on the elapsed time of the sleep state or the age of the subject. For example, it is known that the deep sleep stage tends to appear in the beginning of sleep and that its appearance frequency decreases with time. Further, it is also known that the appearance frequency of the deep sleep stage decreases as the age increases. Therefore, in the above-described aspect, in order to make it possible to obtain a correct prediction result as much as possible, the sleep stage determination unit may be configured to easily output a determination that the sleep state of the subject belongs to the sleep stage that tends to appear according to the length of the sleep elapsed time and/or according to the age of the subject, in the plurality of sleep stages. In particular, when the sleep stage determination unit is configured to determine as the sleep state of the subject the sleep stage of which the sleep stage appearance probability determined by the respiratory motion feature and the body motion feature is the highest in the plurality of sleep stages, the sleep stage determination unit may be configured to multiply the sleep stage appearance probability of each of the plurality of sleep stages by a weight according to a tendency of appearance of each of the plurality of sleep stages according to the length of the sleep elapsed time and/or the age of the subject, and to determine as the sleep state of the subject the sleep stage of which the sleep stage appearance probability multiplied by the weight is the highest.

In the above-described aspect, typically, the device may be housed in a housing that is wearable on the body of the subject and is portable. However, for example, it may be configured that the sleep stage determination unit is formed in an arithmetic processing device or a computer that is separate from a housing worn on the body of the subject, that the processing up to the measurement of respiratory motion index values and body motion index values or the processing up to the extraction of an respiratory motion feature and a body motion feature is performed in the housing worn on the body of the subject, and that these values are transferred to the arithmetic processing device or the computer where a sleep stage determination is carried out.

According to the above-described aspect, as described above, since a sleep stage determination is carried out referring to a sleep state value that is calculated using a respiratory motion feature and a body motion feature as variables, the particular sleep stage is not specified only with the occurrence of a significant change in a respiratory motion state or a body motion state of the subject (e.g. the wake stage is not predicted solely by the detection of a significant body motion), and a determination of the sleep stage is made by evaluating the other states comprehensively or integrally. Therefore, for example, compared to the configuration that determines to which of a plurality of sleep stages the sleep state of the subject belongs by separately referring to a respiratory motion feature and a body motion feature in turn as in the conventional similar devices, it is expected that the sleep stage prediction result becomes more accurate (error determination is reduced). The device of the disclosure can be configured to be worn on the chest or abdomen of the subject, thus does not require a large-scale facility, and can be used as a household device or an in-vehicle device.

A sleep state prediction device according to a second aspect of the disclosure includes a first sensor configured to measure respiratory motion index values indicating a respiratory motion state of a subject; a second sensor configured to measure body motion index values indicating a body motion state of the subject; and a computing unit configured to extract a respiratory motion feature from the respiratory motion index values; extract a body motion feature from the body motion index values; calculate a sleep state value based on the respiratory motion feature, the body motion feature, and a sleep state function; determine, based on the sleep state value, to which of a plurality of sleep stages in a sleep state including a wake stage a sleep state of the subject belongs; and output the determined sleep stage of the subject, wherein the sleep state function is adjusted by a learning process using, as training data, data groups including sleep stage determination results by a measurement of a sleep state for calibration, and respiratory motion features and body motion features that are respectively extracted from respiratory motion index values and body motion index values measured simultaneously with the measurement for calibration.

According to the above-described aspect, the sleep stage can be determined more accurately.

BRIEF DESCRIPTION OF THE DRAWINGS

Features, advantages, and technical and industrial significance of exemplary embodiments of the disclosure will be described below with reference to the accompanying drawings, in which like numerals denote like elements, and wherein:

FIG. 5A to FIG. 5C are diagrams showing examples of the results of determinations of a sleep state that are carried out for a subject, wherein FIG. 5A shows the sleep state determination result using PSG, FIG. 5B shows the sleep state determination result according to the embodiment of the sleep state prediction device according to the disclosure, and FIG. 5C shows the result according to a comparative example, wherein a determination of a sleep state is made using only a respiratory motion feature without using a body motion feature.

DETAILED DESCRIPTION OF EMBODIMENTS

Configuration of Device

Figure 1A:
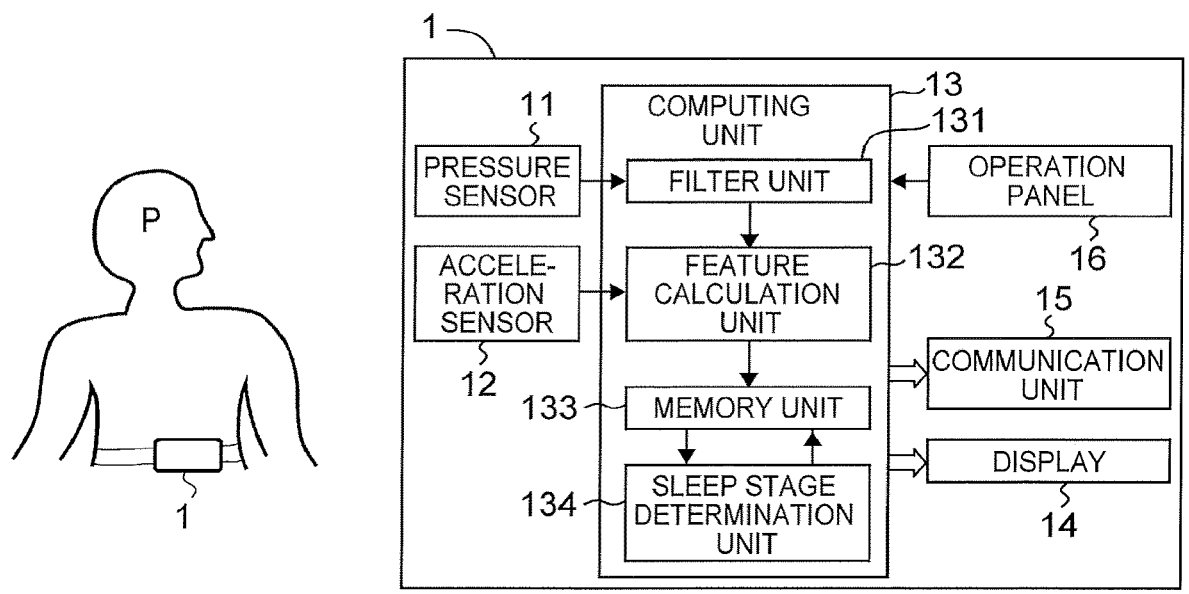
FIG. 1A is a diagram exemplarily showing an embodiment of a sleep state prediction device according to the disclosure, which is wearable on the chest or abdomen of a subject, wherein the configuration inside the sleep state prediction device is shown in the form of a block diagram on the right side.

Referring to FIG. 1A, a sleep state prediction device 1 according to an embodiment of the disclosure has a housing that is wearable on the chest or abdomen of a subject P, and respective units necessary for predicting a sleep state are housed in the housing. In the housing of the device 1, as shown in the form of a block diagram on the right side of FIG. 1A, there are provided a pressure sensor 11 that measures the pressure which changes due to the displacement of the body surface caused by the respiratory motion of the subject, an acceleration sensor 12 that measures the acceleration value which changes due to the body motion of the subject, a computing unit 13 that receives the outputs of the sensors (the pressure sensor 11 and the acceleration sensor 12) and makes a determination on the sleep state of the subject in a later-described manner, a display 14 that displays an output value of the computing unit 13 and/or an operating state of the device, a communication unit 15 that transmits the output value of the computing unit 13 to an external device or facility, and an operation panel 16 that allows the subject or a user to instruct/operate the device.

The pressure sensor 11 may be an arbitrary sensor, such as a sensor using a piezoelectric element, that is used for measuring respiratory waveform data in this field. The pressure sensor 11 measures as a pressure value the displacement of the body surface due to contraction and expansion of the chest or abdomen of the subject caused by the respiratory motion. In this regard, since it is necessary to measure the displacement of the body surface caused by the respiratory motion as a change in pressure value, the pressure sensor 11 is pressed against the body surface of the subject by a band, a belt, or the like to an extent that does not hinder the respiratory motion. The acceleration sensor 12 is a sensor that measures the acceleration value which changes due to the body motion of the subject as described above, while the direction of the body motion is arbitrary, and therefore, a three-axis acceleration sensor may be used.

During the measurement of the sleep state, the pressure values measured by the pressure sensor 11 and the acceleration values measured by the acceleration sensor 12 are sequentially input to the computing unit 13, and based on the pressure values and the acceleration values, the computing unit 13 determines a sleep stage via a series of computing processes in a later-described manner. The computing unit 13 may be a normal small computer device including a microcomputer, a memory or a flash memory, and so on. In particular, in the case of the sleep state prediction device of this embodiment, the computing unit 13 includes a filter unit 131 that extracts, based on time-series data of pressure values from the pressure sensor 11, components in a band of a pressure change due to the displacement of the body surface caused by the respiratory motion of the subject, a feature calculation unit 132 that extracts a respiratory motion feature and a body motion feature from time-series data of pressure values and acceleration values, i.e. time-series data of respiratory motion index values and body motion index values, in a manner which will be described in detail later, a sleep stage determination unit 134 that calculates a sleep state value using the respiratory motion feature and the body motion feature and predicts a sleep stage based on the sleep state value, and a memory unit 133 that stores the respiratory motion feature, the body motion feature, the sleep stage prediction result, and so on. It may be configured that inputs from the operation panel 16 are given to the computing unit 13 such that instructions for start and end of the measurement of the sleep state and other arbitrary instructions by the subject or user are input to the computing unit 13 by operating the operation panel 16. It may be configured that the sleep stage determination result, the output values of the sensors 11 and 12, intermediate values obtained in a series of computing processes, and other information that are given by the computing unit 13 are displayed on the display 14 connected to the computing unit 13, or are transmitted to an external computer device or facility via the communication unit 15. Since the respiratory motion feature, the body motion feature, the sleep stage prediction result, and so on also become time-series data, if these data are displayed on the relatively small housing 1, there is a case where it is troublesome for the subject or user to visually confirm the data. Therefore, it may be configured that the respiratory motion feature, the body motion feature, the sleep stage prediction result, and so on are not displayed on the housing 1, but are displayed or printed in the external computer device or facility. In this case, it is not necessary to provide a display for displaying the respiratory motion feature, the body motion feature, the sleep stage prediction result, and so on. It is to be understood that the operations of the computing unit 13 and the other units in the device are created by execution of a program stored in the memory unit 133.

Figure 1B:
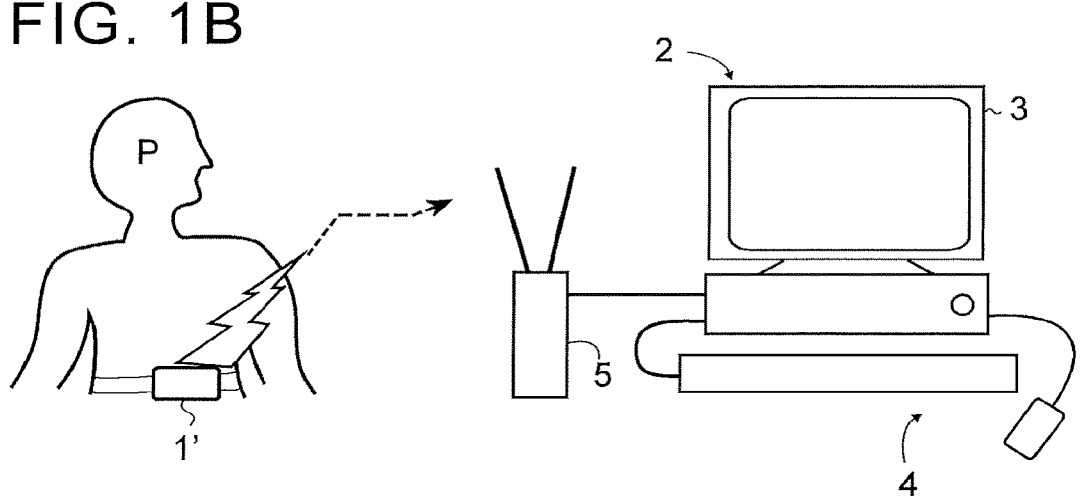
FIG. 1B is a diagram exemplarily showing another embodiment of a sleep state prediction device according to the disclosure, wherein there is shown a case where part of computing processes for determining a sleep state is executed by an external computer device.

As another embodiment of a sleep state prediction device according to the disclosure, as exemplarily shown in FIG. 1B, it may be configured that only the sensors 11 and 12, the sensors 11 and 12 and the filter unit 131, or the sensors 11 and 12, the filter unit 131, and the feature calculation unit 132 in the device are housed in a wearable housing 1' and that the other computing processes are executed by a computer device 2 separate from the housing P. The computer device 2 may be a device including, in a normal manner, a monitor 3, an input device 4 such as a keyboard and a mouse, and a communication device 5 that receives a signal transmitted from the housing 1'. In this case, signals indicating pressure values (or filtered pressure values) and acceleration values obtained on the subject, or signals indicating a respiratory motion feature and a body motion feature may be input to the computer device 2 via the communication device 5 from a communication unit in the housing 1', thereby executing a series of computing processes for determining a sleep stage.

Operation of Device (i) Summary of Operation In the sleep state prediction device 1 according to the embodiment of the disclosure, to give a brief description, as described in the column of "SUMMARY", a respiratory motion feature and a body motion feature that are correlated to a sleep state are extracted at a predetermined time interval from time-series data of respiratory motion index values and body motion index values that are obtained by the measurement on the body of the subject, then a sleep state value is calculated by a sleep state function using the extracted respiratory motion feature and body motion feature as variables, and based on the sleep state value, a determination of a sleep stage of the subject is made per the predetermined time interval. In such a configuration, particularly in this embodiment, as a sleep state value that is calculated by the sleep state function, the probabilities (appearance probabilities) of appearance of a plurality of sleep stages in the sleep state when a pair of a respiratory motion feature and a body motion feature are given are calculated, and in principle, the sleep stage having the highest value among those appearance probabilities is determined to be the sleep stage of the subject when the pair of respiratory motion feature and body motion feature are obtained. As described above, the sleep state function that gives the sleep state value is a function that is adjusted in advance by a learning process using, as training data, data groups including sleep stage determination results obtained by a measurement that can determine a sleep stage more accurately, such as the measurement by PSG, and respiratory motion features and body motion features that are respectively extracted from pressure values (respiratory motion index values) and acceleration values (body motion index values) measured simultaneously with such a measurement, thereby making it possible to determine a sleep stage of the subject as accurate as possible. In particular, in this embodiment, the learning process is carried out according to the theory of the least-squares probabilistic classifier (Sugiyama et al., "LEAST-SQUARES PROBABILISTIC CLASSIFIER: A COMPUTATIONALLY EFFICIENT ALTERNATIVE TO KERNEL LOGISTIC REGRESSION" Proceedings of International Workshop on Statistical Machine Learning for Speech Processing (IWSML 2012), pp. 1-10, Kyoto, Japan, Mar. 31, 2012).

According to the operation of the device of the disclosure described above, since the sleep stage is determined based on the sleep state value that is calculated by the sleep state function using the respiratory motion feature and the body motion feature as variables, the determination of the sleep stage is not made by referring to the magnitude or increase/decrease of a single feature, but is made by comprehensively referring to the respiratory motion feature and the body motion feature, so that the sleep stage is expected to be determined more accurately in the situation where the correspondence relationship between a feature and a sleep stage is complicated. In the configuration described above, when a respiratory motion feature and a body motion feature are given, a single sleep stage is not directly specified, but the appearance probabilities of a plurality of sleep stages are first calculated, so that it is advantageous in that it is possible to evaluate the appearance probabilities of the respective sleep stages, i.e. the ease of appearance of the respective sleep stages, in other words, the certainty of a determination on the appearance of a certain sleep stage. Hereinbelow, the processes from the measurement of respiratory motion index values and body motion index values to a determination of a sleep stage and the learning process of a sleep state function that is used therein will be described.

Figure 2A:
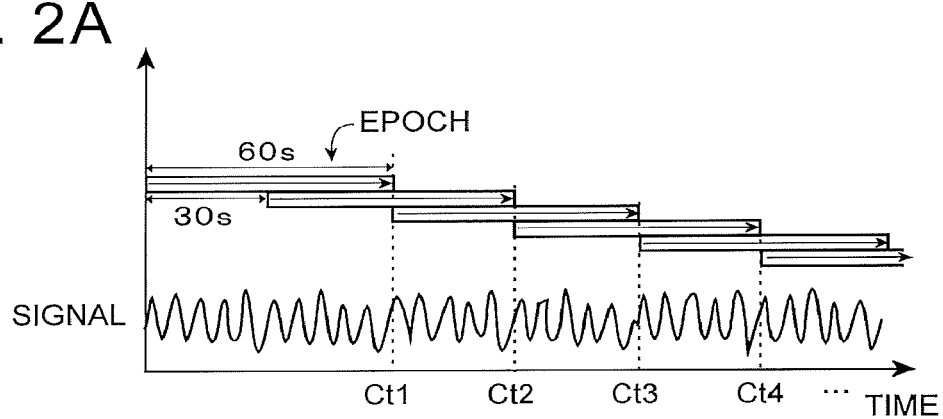
FIG. 2A is a diagram for explaining the timing of signal processing in the embodiment of the sleep state prediction device according to the disclosure.

(1) Timing of Process of Determination of Sleep Stage In general, data that are measured on the subject are sequentially obtained in a determination of a sleep stage, while, as a feature (amount correlated to a sleep stage) in the data that is used for determining the sleep stage, a statistic per predetermined time interval (epoch) in time-series measured value data is employed. This may also apply to a determination of a sleep stage in this embodiment. Specifically, for example, as exemplarily shown in FIG. 2A, a respiratory motion feature and a body motion feature are calculated per epoch in data (signals) of respiratory motion index values (pressure values) and body motion index values (acceleration values) that are measured in time series. As shown in FIG. 2A, each epoch may overlap (or may not overlap) with prior and subsequent epochs along the time axis. In the case of the example of FIG. 2A, each epoch is 60 seconds, but since each epoch overlaps with the prior and subsequent epochs for 30 seconds, respectively, the respiratory motion feature and the body motion feature are calculated at time points (Ct1, Ct2, . . . ) with an interval of 30 seconds. In this embodiment, a determination of a sleep stage may also be made per time point of the calculation of the respiratory motion feature and the body motion feature (it is to be understood that such a determination may be made at a different timing). Therefore, the determination result per epoch is output at a time point of termination of each epoch.

(2) Calculation of Respiratory Motion Feature and Body Motion Feature According to experiments and studies by the inventors of the disclosure, it has been found that respiratory motion features and a body motion feature that are calculated per epoch are advantageously used as features correlated to a sleep stage.

(i) As respiratory motion features, four features, i.e. "mean respiratory rate", "respiratory coefficient of variation", "amplitude coefficient of variation" and "autocorrelation peak ratio", that are extracted from respiratory waveform in time-series pressure data are advantageously used. As described above, since variation components other than the pressure change due to the displacement of the body surface caused by the respiratory motion are included in the output from the pressure sensor 11, first, before extracting the respiratory motion features, components in a band of the pressure change due to the displacement of the body surface caused by the respiratory motion are extracted (filtering process) by the filter unit 131, and the following respiratory motion features are extracted in the pressure data (respiratory waveform data) after the filtering process. The definition of each feature is as follows (see FIG. 2B). The mean value and the standard deviation are the mean value and the standard deviation of values in an epoch.

Figure 2B:
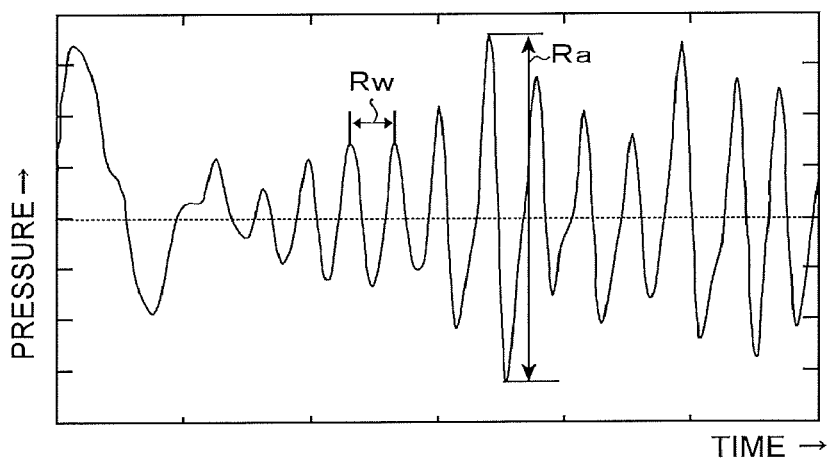
FIG. 2B is a diagram showing respiratory waveform data (time-series data of respiratory motion index values) that are obtained in the embodiment of the sleep state prediction device according to the disclosure, and explaining the definition of a respiratory motion feature that is used for determining a sleep state.

(a) Mean Respiratory Rate=60 [sec]/mean value of respiratory waveform peak intervals [sec]: Since, in respiratory waveform data, a peak interval Rw [sec] is a time required for one respiration, the respiratory rate per minute in the case of the peak interval Rw becomes 60/Rw (hereinafter simply referred to as a "respiratory rate"). Therefore, herein, the mean value of respiratory rates in an epoch is calculated by 60/(mean value of a time required for one respiration). (b) Respiratory Coefficient of Variation=standard deviation of respiratory rates/mean respiratory rate: The standard deviation of respiratory rates is a standard deviation of respiratory rates 60/Rw in an epoch. (c) Amplitude Coefficient of Variation=standard deviation of amplitudes/mean amplitude: As shown in FIG. 2B, the amplitude is a difference Ra between an upper peak and a lower peak, the mean amplitude is a mean value of Ra in an epoch, and the standard deviation of amplitudes is a standard deviation of Ra in an epoch. (d) Autocorrelation Peak Ratio: In an autocorrelation function value ($\tau$) ($\tau$ is a correlation time) of values obtained by subtracting the mean of pressure data in an epoch from the pressure data in the epoch, the autocorrelation peak ratio is a value obtained by dividing a peak value of a peak, which appears first (when $\tau=\tau p$) as seen from $\tau=0$, by an autocorrelation function G (0) and normalizing it.

Figure 2C:
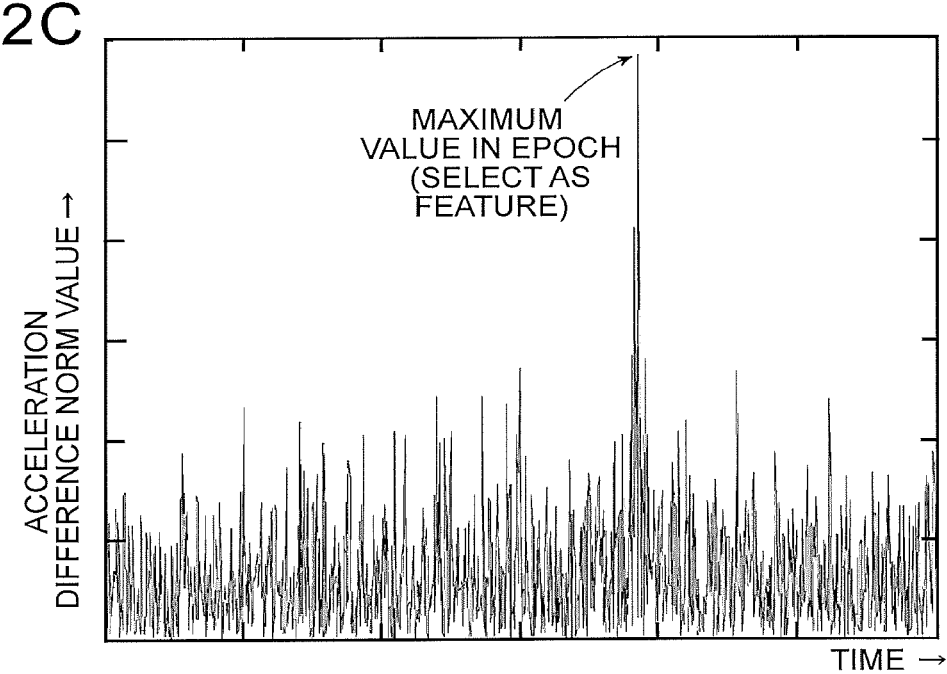
FIG. 2C is a diagram showing time-series data of acceleration difference norms that are calculated from acceleration values (body motion index values) that are obtained in the embodiment of the sleep state prediction device according to the disclosure.

(ii) As a body motion feature, the maximum value, in an epoch, of acceleration difference norms that are calculated by the following formula is advantageously used. Acceleration Difference Norm=$\{(ax_t-ax_{t-1})^2+(ay_t-ay_{t-1})^2+(az_t-az_{t-1})^2\}^{1/2}$, where $ax_t$, $ay_t$, and $az_t$ are respectively acceleration values at a time point t in x-axis, y-axis, and z-axis directions. As shown in FIG. 2C, the maximum value of acceleration difference norms is such that acceleration difference norms are first calculated per epoch and then the maximum value thereof is selected.

(iii) Normalization of Respiratory Motion Features and Body Motion Feature The four respiratory motion features and the body motion feature are calculated per epoch in data obtained in one-time sleep state measurement (in principle, from a time when a measurement start instruction is given to a time when a measurement end instruction is given (see a later-described column of the flow of measurement)). Herein, according to experiments and studies by the inventors of the disclosure, it has been found that, with respect to the respiratory motion features and the body motion feature that are respectively calculated by the above-described formulae, inter-individual differences and intra-individual differences in the values of the respiratory motion features and the body motion feature affect a later-described determination of a sleep stage. Therefore, in order to eliminate such an influence as much as possible, normalized values of the respiratory motion features and the body motion feature are used as features for determining a sleep stage. Specifically, the normalization may be performed, for example, by subtracting, from the respiratory motion features and the body motion feature of each epoch, the medians of the corresponding features of all the epochs, respectively. It has been found that when the features subjected to such normalization are used, it is possible to favorably achieve a determination of a sleep stage.

As described above, in this embodiment, features that are different from the features listed above may be employed, and it is to be understood that even such a case belongs to the scope of the disclosure. In this embodiment, at least five amounts, which is relatively large in number compared to the conventional similar devices, are used as the features that are referred to for determining the sleep stage, and therefore, noise in the measured data hardly affects the determination of the sleep stage, so that the determination result is expected to be stable. Further, in particular, the body motion feature is calculated from the acceleration values and thus is a value that not only simply indicates the presence or absence of a body motion, but also has a continuous magnitude, and therefore, when determining to which of a plurality of sleep stages the sleep state of the subject corresponds, the magnitude of the body motion is also referred to, so that a more accurate determination of the sleep stage is expected to be made possible.

(3) Sleep State Function and Calculation of Appearance Probabilities of Sleep Stages As described above, in this embodiment, when respiratory motion features and a body motion feature (after normalization—hereinafter, unless otherwise stated, the features are, all, values after the normalization) are given, the appearance probabilities of respective sleep stages in the state where the respiratory motion features and the body motion feature are given are calculated by a sleep state function using the respiratory motion features and the body motion feature as variables. In this embodiment, as described above, the sleep state function may be adjusted by the learning process according to the theory of the least-squares probabilistic classifier. Specifically, the sleep state function may be defined as follows.

First, a feature vector X=(x1, x2, x3, x4, x5) . . . (1a) formed by values of respiratory motion features and a body motion feature is defined. Herein, xi (i=1 to 5) are the respiratory motion features and the body motion feature. In the case of this embodiment, x1=mean respiratory rate, x2=respiratory coefficient of variation, x3=amplitude coefficient of variation, x4=autocorrelation peak ratio, and x5=maximum value of acceleration difference norms. Further, sleep stages (classes) to be determined are set as y∈{Wake, REM, Light, Deep} . . . (1b), where Wake: wake stage, REM: REM sleep stage, Light: shallow sleep—non-REM sleep stages I, II, Deep: deep sleep—non-REM sleep stages III, IV (or may be set finer or rougher).

Herein, when there are N training data groups Xtn (n=1 . . . N) (n is a symbol of a data point), an appearance probability p(y/X) of each sleep stage y when the feature vector X is obtained, i.e. a sleep state function, is given as follows according to the theory of the least-squares probabilistic classifier. p(y/X)=[max(0, q(y|X:$\theta_y$))]/$\Sigma$[max(0, q(ya|X:$\theta_{ya}$))] . . . (2), where ya is a symbol of the sleep stages, and E is the sum total of ya=Wake, REM, Light, Deep. The appearance probability p(y/X) corresponds to a posterior probability of appearance of the sleep stage y in the case of the feature vector X. In the formula (2), q(y|X:$\theta_y$) corresponds to the sum total of values each indicating a degree of state approximation that depends on the distance between a position of each point of the training data being the sleep stage y and a position of a point of the feature vector X in a space in which the feature vector is spanned (feature space), and is specifically expressed as follows. q(y|X:$\theta_y$)=$\Sigma\theta$y,n·$\varphi$n(X) . . . (3) ($\Sigma$ is the sum total for the training data n=1 ... N), where $\theta_{y,n} \cdot \varphi_n(X)$ ... (4) is a function (basis function) giving a value indicating a basis of a degree of approximation between a point of the feature vector X and a point Xtn of the training data. $\varphi_n(X)$ is a Gaussian basis function that is defined by $\varphi_n(X)=\exp(-L_n^2/2\sigma^2)$ ... (5) using a distance $L_n=\|X-Xtn\|$ between a point of the feature vector X and a point Xtn of the training data in the feature space, $\theta_{y,n}$ is a coefficient parameter that determines the height of the basis function, and $\sigma$ is a parameter that determines the width of the basis function (as will be described later, $\sigma$ is one of hyper parameters).

Figure 3A:
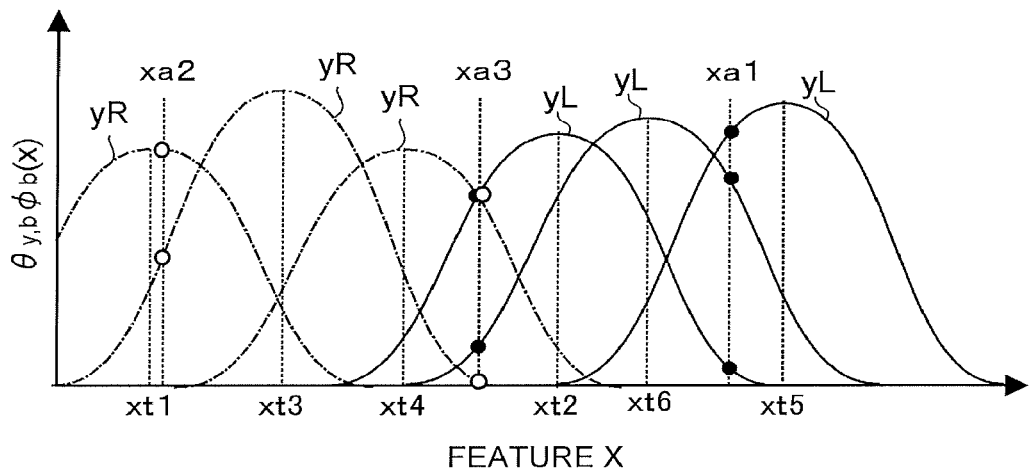
FIG. 3A is an exemplary diagram for explaining the principle of a sleep state function that is used for determining a sleep state in the embodiment of the sleep state prediction device according to the disclosure, wherein there are shown basis functions that are set for data points of training data (training data points xti) (functions indicating the degrees of state approximation between arbitrary points (features xai) and the training data points)

To give a brief description, the reason why the appearance probability p(y/X) is determined from the basis functions $\theta_{y,n} \cdot \varphi_n(X)$ of the points Xtn of the training data is as follows. Referring to FIG. 3A, when, for example, feature vectors xt1, xt3, and xt4 being a sleep stage yR and feature vectors xt2, xt5, and xt6 being a sleep stage yL are given as points Xtn of the training data (while the feature vector is shown to be one-dimensional, it is actually multidimensional and is five-dimensional in this embodiment), it can be assumed that a region of an approximate state is distributed around each point of the training data and that the shape of the basis becomes higher as the distance is closer. Assuming that the basis function of the point of the training data has a profile in the format of the formula (4) (in a space spanned with the features and the degree of state approximation) as shown by a solid line or a one-dot chain line in FIG. 3A, it can be considered that, for example, the degree of approximation between a state of a point of a feature vector xai obtained by measurement and a state of the point of the training data is a value of the basis function of the point of the training data at the position of the feature vector xai. For example, in the case of a feature vector xa1 (black circles in FIG. 3A), since the feature vector xa1 is close to the feature vectors xt2, xt5, and xt6 being the sleep stage yL, significant values are given in the basis functions thereof, while since the feature vector xa1 is far from the feature vectors xt1, xt3, and xt4 being the sleep stage yR, values in the basis functions thereof are substantially 0. Therefore, it can be considered that the feature vector xa1 has a high degree of approximation to the state of the sleep stage yL. Likewise, in the case of a feature vector xa2 (white circles in FIG. 3A), since significant values are given in the basis functions of the feature vectors xt1 and xt3 being the sleep stage yR and values are substantially 0 in the other basis functions, it can be considered that the feature vector xa2 has a high degree of approximation to the state of the sleep stage yR. Further, in the case of a feature vector xa3, while values in the basis functions of the feature vector xt2 being the sleep stage yL and the feature vector xt4 being the sleep stage yR are approximately equal to each other, a value of the basis function of the feature vector xt6 being the sleep stage yL is greater than a value of the basis function of the feature vector xt3 being the sleep stage yR, and therefore, it can be considered that the feature vector xa3 has a relatively high degree of approximation to the state of the sleep stage yL.

In this way, when a feature vector x is obtained, basis functions $\theta_{y,n} \cdot \varphi_n(X)$ being values indicating the degrees of state approximation to the points Xtn of the training data are added together per sleep stage as shown by the formula (3) to calculate the sum total of the degrees of approximation $q(y|X:\theta_y)$ per sleep stage, and further, by dividing this value by the sum total of the degrees of approximation for all the sleep stages, it is possible to calculate a probability that the state of the feature vector x is the state of each sleep stage, i.e. an appearance probability p(y/X) of each sleep stage when the feature vector x is obtained. The reason why computation to select a maximum value between a 0 value and $q(y|X:\theta_y)$ is executed in the formula (2) is for setting a value to 0 when $q(y|X:\theta_y)$ becomes a negative value. A specific example of the learning process for the sleep state function will be described later.

Figure 3B:
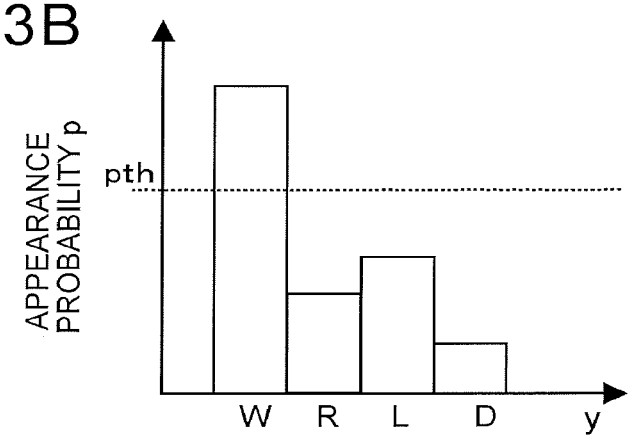
FIG. 3B is a diagram showing appearance probabilities of a plurality of sleep stages in a sleep state that are calculated when a certain feature vector (a pair of a respiratory motion feature and a body motion feature) is given, wherein there is shown a state in which the highest probability exceeds a predetermined threshold value.
Figure 3C:
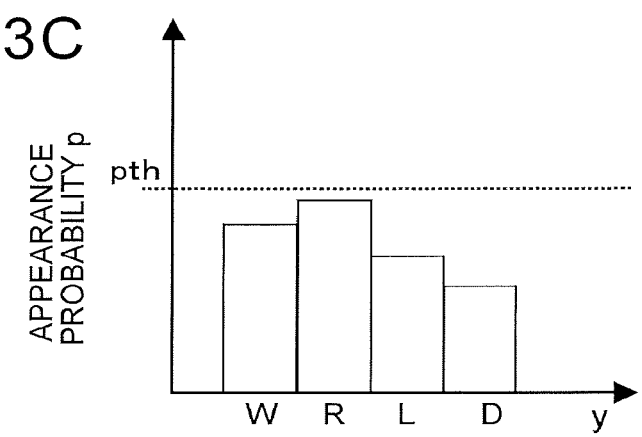
FIG. 3C is a diagram similar to FIG. 3B, wherein there is shown a case where the highest probability does not exceed the predetermined threshold value and a sleep stage is determined to be unclear.

(4) Determination of Sleep Stage According to the formula (2), the appearance probability of each of a plurality of sleep stages is calculated when a feature vector is obtained. Therefore, the sleep stage whose probability is the highest among them can be determined to be the sleep stage of the subject. In this regard, for example, as shown in FIG. 3B, when the appearance probability of the particular sleep stage is outstanding, that sleep stage can be determined to be the sleep stage of the subject with sufficient certainty. However, as shown in FIG. 3C, when the appearance probability of the sleep stage with the highest probability is not so high compared to the appearance probabilities of the other sleep stages, the certainty of that sleep stage as the sleep stage of the subject is low. In such a case, if the particular sleep stage is determined to be the sleep stage of the subject, the lowering of the determination accuracy may occur. In fact, as described above, the sleep state of a human being is continuous such that there is a possibility that the sleep stage cannot be specified essentially clearly in a region between the defined sleep stages or on the way of transition from one to another. Therefore, in this embodiment, in the determination of the sleep stage, when the appearance probability of the sleep stage with the highest probability exceeds a predetermined threshold value pth (FIG. 3B), that sleep stage is determined to be the sleep stage of the subject, while when the appearance probability of the sleep stage with the highest probability does not exceed the predetermined threshold value pth (FIG. 3C), it may be determined that the sleep stage of the subject is unclear, or it may be determined that the sleep stage of the subject is one of the two high-probability sleep stages.

By referring to the appearance probabilities of the sleep stages that are calculated as described above, it is possible to predict a falling-asleep time. Specifically, among the appearance probabilities of the sleep stages described above, the sum of the appearance probabilities of the sleep stages Light and Deep indicates the appearance probability of non-REM sleep. Therefore, when the sum of the appearance probabilities of the sleep stages Light and Deep first exceeds a predetermined threshold value from the start of the measurement, it can be determined that the subject has fallen asleep, and accordingly, it is possible to predict a falling-asleep time when the subject actually has fallen asleep. In this case, it may be determined that the subject has fallen asleep when the state in which the sum of the appearance probabilities of the sleep stages Light and Deep is above the predetermined threshold value is continued a plurality of times (e.g. over two epochs). With this configuration, an predicted value of a falling-asleep time is expected to be stable.

Further, since the sleep stage determination result by this embodiment is an prediction based on the respiratory motion features and the body motion feature, there may occur a case in which a result is obtained that the sleep stage transitions harder than an actual sleep stage of the subject or that the sleep stage transitions unnaturally. Therefore, after making a determination of the sleep stage per epoch in one-time sleep state measurement and obtaining time-series sleep stage determination data, a median filtering process or another smoothing process may be applied to the determination data. With this configuration, the transition of the sleep stage that is unnatural or harder than normal is removed from the determination result, so that it is expected that the transition of the sleep stage closer to actual transition of the sleep stage of the subject is obtained. When the falling-asleep time is predicted based on the sum of the appearance probabilities of the sleep stages Light and Deep as described above, since it is considered that the subject is awakened before the falling-asleep time, all epochs from the start of the measurement to an epoch determined to be a falling-asleep epoch may be corrected to the sleep stage Wake, or the REM sleep stage predicted in a predetermined period (e.g. 30 minutes) from an epoch determined to be a falling-asleep epoch may be corrected to the sleep stage Light. With this configuration, an effect can be expected to suppress the influence of the hard change of the sleep stage that occurs due to noise of the sensors 11 and 12.

(5) Correction of Determination of Sleep Stage As described in the column of "SUMMARY", it is known that, in general, the appearance frequencies of the sleep stages change depending on the sleep elapsed time or the age. Specifically, it is known that, among the sleep stages, the non-REM sleep stages III, IV indicating the deep sleep (Deep) tend to appear in the beginning of sleep and then gradually become harder to appear. Further, it is known that the non-REM sleep stages III, IV relatively tend to appear in the young and become harder to appear as the age increases. Therefore, in the determination of the sleep stage of this embodiment described above, a correction process may be carried out such that the sleep stage that tends to appear according to the length of the sleep elapsed time and/or according to the age of the subject is easily determined to be a sleep state of the subject.

Specifically, first, in the correction of the determination of the sleep stage according to the length of the sleep elapsed time, in the sleep state function of the formula (2), a correction may be performed to multiply p(y/X) of the sleep stage, whose appearance frequency changes according to the length of the sleep elapsed time, by a weight wty that depends on the length of the sleep elapsed time from the falling asleep, as follows. $p(y/X) = wty[\max(0, q(y|X:\theta_y))]/\theta[\max(0, q(ya|X:\theta_{ya}))]$ ... (2a). According to the knowledge up to now, since the appearance frequency of the deep sleep decreases as the length of the sleep elapsed time increases, a weight wt,deep for the deep sleep may be set as follows. When the elapsed time from the falling asleep is less than 4 hours, wt,deep=1.0. When the elapsed time from the falling asleep is 4 hours or more, wt,deep=0.9. It is to be understood that a weight wty may be set also for the other sleep stages based on appearance frequencies according to the length of the elapsed time. The value of the weight wty may be changed continuously according to the length of the elapsed time. When the weight wty is used, the time in time-series pressure or acceleration data may be referred to as the sleep elapsed time from the falling asleep, thereby determining the value of the weight wty.

Also in the correction of the determination of the sleep stage according to the age of the subject, similarly to the above, in the sleep state function of the formula (2), a correction may be performed to multiply p(y/X) of the sleep stage, whose appearance frequency changes according to the age of the subject, by a weight way that depends on the age of the subject, as follows. $p(y/X) = way[\max(0, q(y|X:\theta_y))]/\theta[\max(0, q(ya|X:\theta_{ya}))]$ ... (2b). According to the knowledge up to now, since the appearance frequency of the deep sleep decreases as the age increases, a weight wa,deep for the deep sleep may be set as follows. wa,deep=1.2 ... 10's, wa,deep=1.1 ... 20's, wa,deep=1.0 ... 30's, wa,deep=0.9 ... 40's, wa,deep=0.8 ... 50's. It is to be understood that a weight way may be set also for the other sleep stages based on appearance frequencies according to the age. The value of the weight way may be changed continuously according to the age. When the weight way is used, the configuration for inputting the age of the subject from the operation panel 16 is provided in the device, and by referring to the input age, a weight way according to that age is used in computation of the appearance probability of the formula (2b).

According to the correction of the sleep state function using the weight wty or the weight way, since the sleep stage whose appearance frequency becomes high according to the situation is relatively easily determined, further improvement in the accuracy of determination of the sleep stage is expected. The weight wty and the weight way may be used simultaneously.

(6) Learning Process for Sleep State Function In the learning process for the sleep state function, specifically, according to the theory of the least-squares probabilistic classifier, all coefficient parameters θy,n of the basis functions of the points of the training data are determined by the following formula (superscript T indicates a transposed matrix). $\Theta y = (\Psi^T \Psi + \rho I_N)^{-1} \Psi^T \Pi_y$ ... (6), where $\Theta y = (\theta_{y,1}, \theta_{y,2}, \ldots, \theta_{y,N})^T$ $\Psi = (\Phi(Xt1), \ldots \Phi(XtN))^T \Phi(X) = (\varphi 1(X) \ldots \varphi n(X) \ldots \varphi N(X))^T \Pi y = (\pi_{y,1}, \pi_{y,2}, \ldots, \pi_{y,N})^T \pi_{y,n} = 1$ (when yn=y); $\pi_{y,n}=0$ (when not yn=y).

σ in the formula (5) and ρ in the formula (6) are hyper parameters and are determined by the following learning sequence. (i) When data sets of N training data groups are given, the data sets are divided into training data sets and verification data sets. For example, 80% data sets are used for learning, while the remaining is used for verification. (ii) Candidates of hyper parameters are prepared, and using the candidates, computation of the formula (6) using the training data sets is executed to set a sleep state function. (iii) The verification data sets are input to the sleep state function obtained in (ii) to evaluate the performance. The evaluation of the performance may be performed in an arbitrary manner. For example, the performance may be arbitrarily evaluated by referring to the accuracy rate of the sleep stage determination results in the case where the verification data sets are input to the sleep state function (assuming that the determination result by the verification data sets is correct), or referring to whether or not the transition of the sleep stage is normal. In this way, when the sleep stage determination results using a pair of hyper parameter candidates are achieved, (i) to (iii) described above are repeatedly carried out using another pair of hyper parameter candidates. This operation may be carried out until a proper pair of hyper parameters are searched out. In the search for a proper pair of hyper parameters, a plurality of pairs of hyper parameters may be prepared in advance, and among the prepared pairs of hyper parameters, the pair whose performance evaluation result is the most excellent (e.g. whose accuracy rate is the highest) may be selected as a proper pair of hyper parameters. Alternatively, the above-described sequence may be repeated by changing a pair of hyper parameters, and when saturation of the accuracy rate is observed or when the accuracy rate exceeds a predetermined threshold value, that pair of hyper parameters may be selected as a proper pair of hyper parameters.

In this way, when the pair of hyper parameters to be used in the formula (6) are determined, using that pair of hyper parameters and using all the data sets of the N training data groups (the total of the training data sets and the verification data sets), Θy (the coefficient parameters θy,n of the basis functions) are calculated by the formula (6). Calculated Θy are stored in the memory unit 133 of the device and are used to calculate an appearance probability of the formula (2) in actual measurement of the sleep state of the subject.

(7) Modification of Learning Process When Training Data is Imbalanced Data It is known that when the ratio of the sleep stages in the training data that is used in the learning process described above is imbalanced, the prediction accuracy is lowered. In fact, in general, in the sleep state of a human being, it is known that the appearance frequency of the shallow sleep—non-REM sleep stages I, II is high, while the appearance frequency of the wake stage and the appearance frequency of the deep sleep—non-REM sleep stages III, IV are low. Therefore, when the ratio of the sleep stages in the training data is imbalanced, i.e. the data sets of the training data are sets of "imbalanced data", the learning process may be modified to correct it.

The learning process that corrects such "imbalanced data" may be carried out as follows. (i) In the training data groups, the number of data of the sleep stage (class) with the least appearance frequency is examined, and the numbers of data of the other classes are made equal to that number. For example, when the number of data of the sleep stage Deep is the smallest and is 500 data, 500 data are extracted at random from data of each of the other sleep stages. (ii) In addition to the hyper parameters σ and ρ in the formula (6), a weight w_y (w_wake, w_light, w_deep, w_rem) for each sleep stage is introduced as a hyper parameter into the formula (3) as follows. $q(y|X:\theta_y) = \theta y, n \cdot \varphi n(X) \cdot w\_y$ ... (3a). Thereafter, a process similar to the above-described learning process for determining the hyper parameters σ and ρ (repeated execution of (i) to (iii) in (6) Learning Process for Sleep State Function) may be carried out until a proper pair of hyper parameters are searched out.

Flow of Process Operation of Device

Figure 4A:
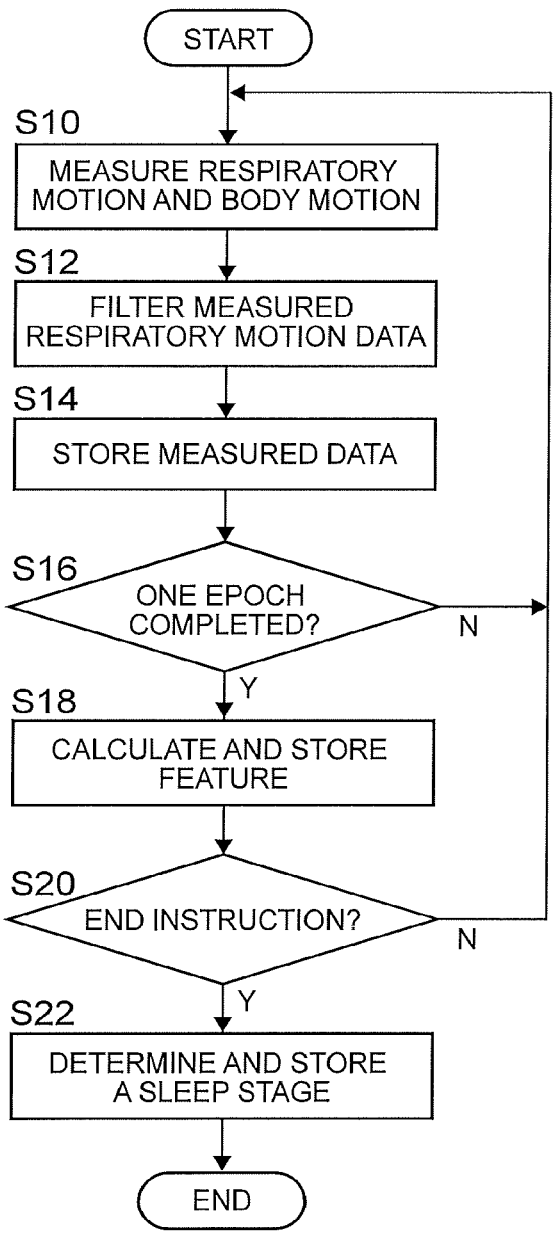
FIG. 4A is a diagram in the form of a flowchart showing the processes from the measurement to a determination of a sleep state in the embodiment of the sleep state prediction device according to the disclosure.
Figure 4B:
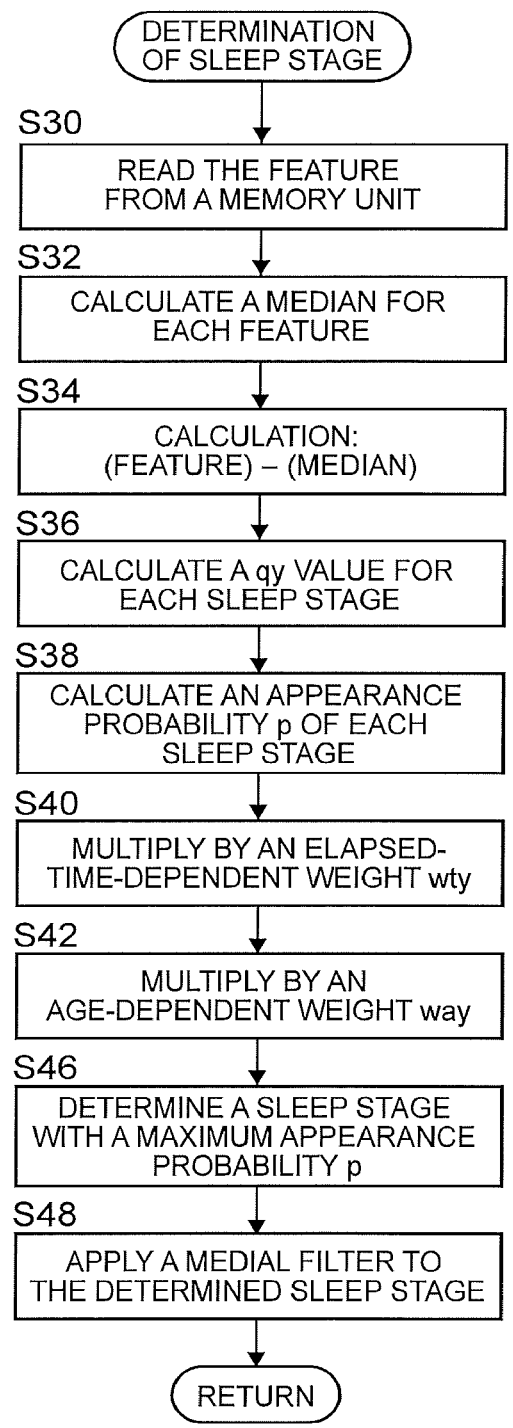
FIG. 4B is a diagram in the form of a flowchart showing the processes of a determination of a sleep stage at step S22 in FIG. 4A.

Referring to FIG. 4A and FIG. 4B, the flow of the process operation in one-time sleep state measurement of the device of this embodiment of the disclosure is as follows. Before using the device, coefficient parameters Θy necessary for calculating an appearance probability p(y/X) by the sleep state function of the formula (2) are calculated in advance using training data according to the above-described learning process, and the calculated coefficient parameters Θy are stored in the memory unit 133 of the computing unit 13.

In one-time sleep state measurement, specifically, referring to FIG. 4A, first, when an instruction for starting a sleep state measurement of the device of this embodiment is given by an operation of the operation panel 16 by the subject or user, until a measurement end instruction is given (step S20), pressure values (respiratory motion index values) and acceleration values (body motion index values) are measured sequentially (step S10), and the measured data are stored in the memory unit 133 (step S14). As described above, a filtering process is applied to the pressure data to extract components in a band of the pressure change caused by the respiratory motion (step S12). Further, every time the measurement for one epoch is completed (step S16), respiratory motion features and a body motion feature are calculated from the time-series measured data in that one epoch and stored in the memory unit 133 (step S18). It is to be understood that the measurement of pressure values and acceleration values continues to be carried out. The calculation of the respiratory motion features and the body motion features may be carried out collectively after the measurement end instruction.

Further, it may be configured that, in the calculation of the respiratory motion features and the body motion feature, when it is determined that the pressure data or the acceleration data is not suitable for calculating the feature, an error flag is set. For example, when the amplitude of respiratory waveform in the pressure data is extremely small in a certain epoch, the reliability of the respiratory motion features is lowered, and therefore, an error flag may be set for that epoch, thereby preventing a determination of the sleep stage from being carried out in the epoch for which the error flag is set. Accordingly, the format of the data that are stored in the memory unit 133 at step S18 is as follows.

TABLE 1

| Epoch | Mean Respiratory Rate | Respiratory Variation Coefficient | Amplitude Variation Coefficient | Autocorrelation Peak Ratio | Acceleration Difference Norm | Error Flag |
|---|---|---|---|---|---|---|
| 1 | | | | | | |
| ... | | | | | | |
| t | | | | | | |
| ... | | | | | | |
| T | | | | | | |

When the measurement end instruction is given, the sleep stage is determined and stored (step S22). Referring to FIG. 4B, in the determination of the sleep stage, after reading the respiratory motion features and the body motion feature from the memory unit 133 (step S30), first, medians of the respiratory motion features and the body motion features from the start of the measurement to the end of the measurement are calculated (step S32), and a normalization computation process is carried out to subtract these medians from the corresponding respiratory motion features and body motion feature, respectively (step S34). Then, using these normalized respiratory motion features and body motion feature, a $q(y|X:\theta_y)$ value for each sleep stage, as described above, is calculated using the formula (3) or (3a) (step S36), and then an appearance probability p(y/X) of each sleep stage is calculated using the formula (2) (step S38). Then, the sleep stage with the highest calculated appearance probability p(y/X) is determined to be the sleep stage of the subject (step S46). When correction of the determination of the sleep stage according to the length of the sleep elapsed time and/or the age of the subject is performed, as described above, a value obtained by multiplying the appearance probability p(y/X) of each sleep stage calculated at step S38 by a weight wty, way according to the length of the sleep elapsed time and/or the age of the subject (see the formulae (2a), (2b)) is used as an appearance probability p(y/X) of each sleep stage (steps S40, S42). It is to be understood that one, both, or neither of the correction of the determination of the sleep stage according to the length of the sleep elapsed time and the correction of the determination of the sleep stage according to the age of the subject may be performed. Preferably, a median filter is applied to the determination result of the sleep stage of the subject for each epoch, so that the final time-series sleep stage determination result is obtained (step S48).

Figure 5A:
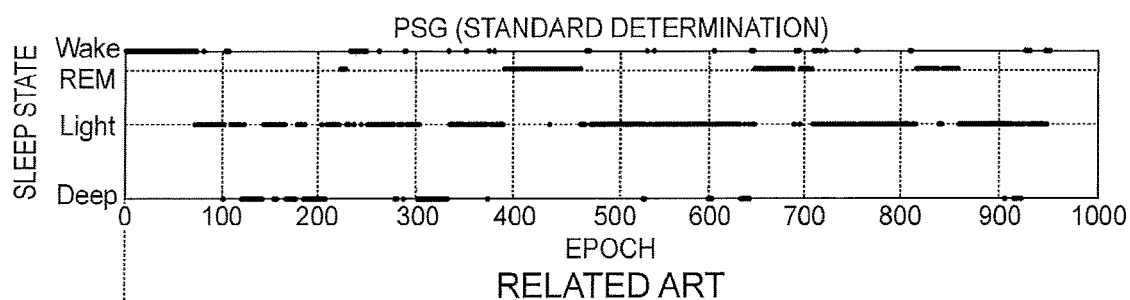
Figure 5B:
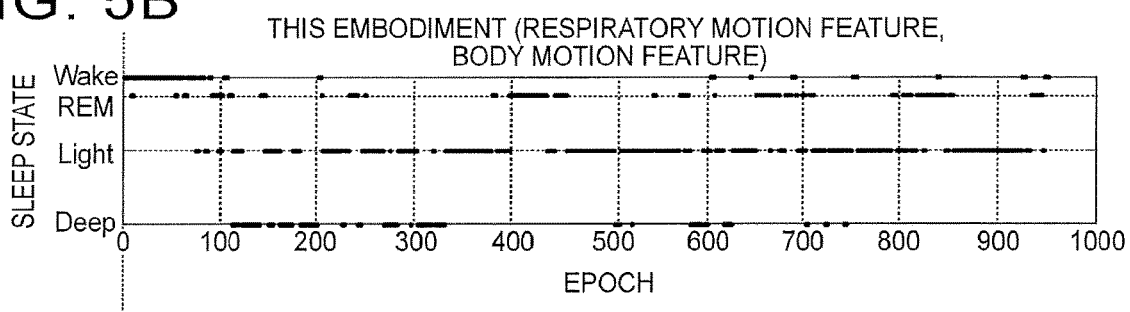
Figure 5C:
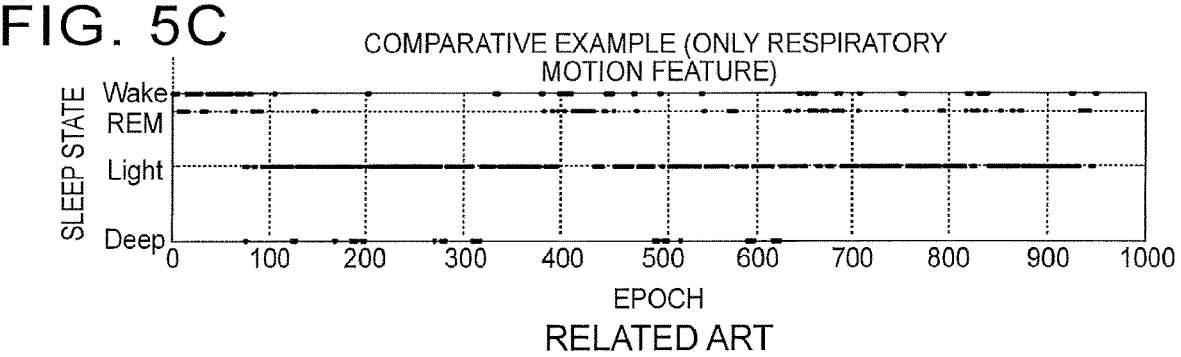

In FIG. 5A to FIG. 5C, there are shown an example of a sleep stage determination result obtained by the series of processes of this embodiment (middle row FIG. 5B), an example of a determination result by PSG carried out simultaneously with the measurement of FIG. 5B (upper row—FIG. 5A), and a comparative example in which a determination of the sleep stage was carried out only by respiratory motion features in the same measured data (lower row—FIG. 5C). Comparing these results, it was observed that the determination result by this embodiment satisfactorily agreed with the determination result by PSG as the standard, while, compared to the comparative example in which the determination was made only by the respiratory motion features without considering the body motion, the determination result by this embodiment was more accurate in the determination of Wake and Deep. This suggests that the determination result with higher accuracy is obtained by comprehensively using the respiratory motion features and the body motion feature in the determination of the sleep stage.

While the disclosure has been described with reference to the embodiments, it is apparent for those skilled in the art that many corrections and changes can easily be made and that the disclosure is not limited only to the embodiments given above by way of example and is applied to various devices without departing from the concept of the disclosure.

What is claimed is:

1. A sleep state prediction device, comprising:
   a first sensor configured to measure, in time series, respiratory motion index values indicating a respiratory motion state of a subject;
   a second sensor configured to measure, in time series, body motion index values indicating a body motion state of the subject, simultaneously with measurement of the respiratory motion state; and
   circuitry configured to:
      extract a respiratory motion feature from time-series data of the measured respiratory motion index values;
      extract a body motion feature from time-series data of the measured body motion index values; and
      determine to which of a plurality of sleep stages, including a wake stage, a sleep state of the subject belongs in a particular epoch based on a sleep state value that is calculated by a sleep state function using the respiratory motion feature and the body motion feature as variables, wherein
   the sleep state function is adjusted by a learning process using, as training data, data groups including sleep stage determination results accepted to be correct, and corresponding respiratory motion features and body motion features,
   the respiratory motion feature is a set including a mean respiratory rate, a respiratory variation coefficient, an amplitude variation coefficient, and an autocorrelation peak ratio per epoch in the time-series measured data of the respiratory motion index values, and the body motion feature includes a maximum value of acceleration difference norms per epoch in the time-series measured data of the body motion index values,
   to determine the maximum value of acceleration difference norms per epoch, the circuitry is configured to determine a plurality of acceleration difference norms per epoch and select a maximum value of the plurality of acceleration difference norms for each epoch,
   the sleep state value that is calculated by the sleep state function is a value that is calculated for each of the plurality of sleep stages and is a sleep stage appearance probability indicating a probability of the sleep state of the subject belonging to each of the plurality of sleep stages in a state where the respiratory motion feature and the body motion feature are obtained, and
   the circuitry is further configured to:
      determine, as the sleep state of the subject in the particular epoch, a sleep stage of the plurality of sleep stages that the sleep stage appearance probability determined by the respiratory motion feature and the body motion feature is the highest among the plurality of sleep stages; and
      predict a falling-asleep time of the subject based on a sum of sleep stage appearance probabilities of non-rapid eye movement sleep stages of the plurality of sleep stages in the particular epoch.

2. The sleep state prediction device according to claim 1, wherein
   the first sensor includes a pressure sensor that is worn on or in contact with a chest or an abdomen of the subject,
   the respiratory motion index value is a pressure value that is measured by the pressure sensor and that changes due to a displacement of a body surface caused by a respiratory motion of the subject,
   the second sensor includes an acceleration sensor that is worn on or in contact with a body of the subject, and
   the body motion index value is an acceleration value that is measured by the acceleration sensor and that changes due to a body motion of the subject.

3. The sleep state prediction device according to claim 1, wherein the sleep state prediction device is housed in a housing that is wearable on the body of the subject and is portable.

4. The sleep state prediction device according to claim 1, wherein
   the respiratory motion feature is a value obtained by subtracting a median of values of features in one-time execution of sleep state prediction among values of features obtained in epochs in the time-series measured data of the respiratory motion index values, and
   the body motion feature is a value obtained by subtracting a median of values of features in one-time execution of sleep state prediction among values of features obtained in epochs in the time-series measured data of the body motion index values.

5. The sleep state prediction device according to claim 2, wherein the circuitry is further configured to:
   extract, from time-series pressure value data measured by the pressure sensor, time-series data of a component of a pressure change due to the displacement of the body surface caused by the respiratory motion of the subject, and
   extract the respiratory motion feature from the extracted time-series data of the component of the pressure change.

6. The sleep state prediction device according to claim 1, wherein the circuitry is further configured to:
   extract the respiratory motion feature and the body motion feature per epoch, and
   determine the sleep stage of the subject per epoch,
   apply a median filtering process to time-series sleep stages, each determined per epoch, and
   determine the sleep stage of each epoch as a result of the filtering.

7. The sleep state prediction device according to claim 1, wherein the sleep state function is adjusted according to a least-squares probabilistic classifier using the training data.

8. The sleep state prediction device according to claim 1, wherein the circuitry is further configured to determine that the sleep state of the subject is unclear when the sleep stage appearance probability of the sleep stage with the highest sleep stage appearance probability does not exceed a predetermined value.

9. The sleep state prediction device according to claim 1, wherein the circuitry is configured to determine the sleep state of the subject according to a length of a sleep elapsed time.

10. The sleep state prediction device according to claim 1, wherein the circuitry is further configured to:
multiply the sleep stage appearance probability of each of the plurality of sleep stages by a weight according to a tendency of appearance of each of the plurality of sleep stages according to a length of a sleep elapsed time, and
determine as the sleep state of the subject the sleep stage of which the sleep stage appearance probability multiplied by the weight is the highest.

11. The sleep state prediction device according to claim 1, wherein the circuitry is configured to determine the sleep state of the subject according to an age of the subject.

12. The sleep state prediction device according to claim 1, wherein the circuitry is configured to:
multiply the sleep stage appearance probability of each of the plurality of sleep stages by a weight according to a tendency of appearance of each of the plurality of sleep stages according to an age of the subject, and
determine as the sleep state of the subject the sleep stage of which the sleep stage appearance probability multiplied by the weight is the highest.

13. The sleep state prediction device according to claim 1, wherein the sleep stage determination results include a determination by polysomnography.

14. The sleep state prediction device according to claim 1, wherein the circuitry is configured to determine each of the plurality of acceleration difference norms based upon a plurality of acceleration values at a time point t in a plurality of directions.

15. The sleep state prediction device according to claim 1, wherein the circuitry is configured to determine each of the plurality of acceleration difference norms based upon a first plurality of acceleration values at a time point t in a plurality of directions and a second plurality of acceleration values at a time point t−1 in the plurality of directions.

16. The sleep state prediction device according to claim 1, wherein the circuitry is configured to correct all epochs, beginning from commencement of the measuring of the respiratory motion state and body motion state of the subject to an epoch containing the failing-asleep time, to be determined as the wake stage.

17. The sleep state prediction device according to claim 16, wherein the circuitry is configured to correct an epoch, determined to be a REM sleep stage in a predetermined period from the epoch containing the falling-asleep time, to be determined as a sleep stage Light.

18. The sleep state prediction device according to claim 1, wherein the circuitry is configured to predict the falling-asleep time based on a sum of sleep stage appearance probabilities of sleep stage Light and sleep stage Deep in the particular epoch.

19. The sleep state prediction device according to claim 18, wherein the circuitry is configured to predict the falling-asleep time when the sum of the sleep stage appearance probabilities of the sleep stage Light and the sleep stage Deep in the particular epoch exceeds a predetermined threshold over more than one epoch.

20. A sleep state prediction device comprising:
a first sensor configured to measure respiratory motion index values indicating a respiratory motion state of a subject;
a second sensor configured to measure body motion index values indicating a body motion state of the subject; and
a computing unit configured to
extract a respiratory motion feature from the respiratory motion index values;
extract a body motion feature from the body motion index values;
calculate a sleep state value based on the respiratory motion feature, the body motion feature, and a sleep state function;
determine, based on the sleep state value, to which of a plurality of sleep stages, including a wake stage, a sleep state of the subject belongs in a particular epoch; and
output the sleep state of the subject, wherein
the sleep state function is adjusted by a learning process using, as training data, data groups including sleep stage determination accepted to be correct, and corresponding respiratory motion features and body motion features,
the respiratory motion feature is a set including a mean respiratory rate, a respiratory variation coefficient, an amplitude variation coefficient, and an autocorrelation peak ratio per epoch in the respiratory motion index values, and the body motion feature includes a maximum value of acceleration difference norms per epoch in the body motion index values,
to determine the maximum value of acceleration difference norms per epoch, the computing unit is configured to determine a plurality of acceleration difference norms per epoch and select a maximum value of the plurality of acceleration difference norms for each epoch,
the sleep state value that is calculated by the sleep state function is a value that is calculated for each of the plurality of sleep stages and is a sleep stage appearance probability indicating a probability of the sleep state of the subject belonging to each of the plurality of sleep stages in a state where the respiratory motion feature and the body motion feature are obtained, and
the computing unit is further configured to:
determine, as the sleep state of the subject in the particular epoch, a sleep stage of the plurality of sleep stages the sleep stage appearance probability determined by the respiratory motion feature and the body motion feature is the highest among the plurality of sleep stages; and
predict a falling-asleep time of the subject based on a sum of sleep stage appearance probabilities of non-rapid eye movement sleep stages of the plurality of sleep stages in the particular epoch.

* * * * *